(12) United States Patent
Baumgartner et al.

(10) Patent No.: US 7,632,271 B2
(45) Date of Patent: Dec. 15, 2009

(54) EXTERNAL MOUNTING DEVICE, PARTICULARLY FOR EXTENSION OF A DISTANCE BETWEEN CLAMPING ELEMENTS

(75) Inventors: Thomas Baumgartner, Derendingen (CH); Andreas Bernhard, Meinisberg (CH)

(73) Assignee: Stryker Trauma S.A. (CH)

( * ) Notice: Subject to any disclaimer, the term of this patent is extended or adjusted under 35 U.S.C. 154(b) by 630 days.

(21) Appl. No.: 11/119,574

(22) Filed: May 2, 2005

(65) Prior Publication Data

US 2006/0177264 A1 Aug. 10, 2006

(30) Foreign Application Priority Data

Feb. 9, 2005 (EP) ................. 05 100 927

(51) Int. Cl.
*A61B 17/00* (2006.01)
(52) U.S. Cl. .......................... 606/55; 606/58
(58) Field of Classification Search ............ 606/54–59, 606/105–105.5, 90, 262; 403/109.3, 319, 403/322.2, 325
See application file for complete search history.

(56) References Cited

U.S. PATENT DOCUMENTS

| | | | |
|---|---|---|---|
| 4,187,841 A * | 2/1980 | Knutson | 606/105 |
| 4,475,546 A | 10/1984 | Patton | |
| 4,628,919 A * | 12/1986 | Clyburn | 606/55 |
| 5,207,676 A | 5/1993 | Canadell et al. | |
| 5,275,599 A | 1/1994 | Zbikowski et al. | |
| 5,314,426 A | 5/1994 | Pohl et al. | |
| 5,330,480 A * | 7/1994 | Meloul et al. | 606/80 |
| 5,454,810 A | 10/1995 | Pohl et al. | |
| 5,549,634 A * | 8/1996 | Scott et al. | 606/170 |
| 5,556,399 A * | 9/1996 | Huebner | 606/80 |
| 5,704,938 A * | 1/1998 | Staehlin et al. | 606/62 |
| 6,245,075 B1 * | 6/2001 | Betz et al. | 606/105 |
| 6,500,177 B1 * | 12/2002 | Martinelli et al. | 606/57 |
| 7,063,706 B2 * | 6/2006 | Wittenstein | 606/90 |
| 2004/0059331 A1 | 3/2004 | Mullaney | |
| 2005/0165404 A1 * | 7/2005 | Miller | 606/80 |

FOREIGN PATENT DOCUMENTS

DE 92 14 550.7 U1 3/1994
FR 2557933 7/1985

* cited by examiner

*Primary Examiner*—Eduardo C Robert
*Assistant Examiner*—Devanie Dufour
(74) *Attorney, Agent, or Firm*—Lerner, David, Littenberg, Krumholz & Mentlik, LLP (57) ABSTRACT

An external fixation device for the extension of the distance between two clamping members of an external fixator has a central internal rod and an outer hollow housing. The internal rod is movable axially. One end of the internal rod projects over the one end of the housing, and serves to fix the one clamping member. An adjusting member is provided disposed at the other end of the housing and is connected with internal rod and/or the outer hollow housing, whereby the axial position of the interior shaft can be adjusted in relation to the housing by means of rotation of the adjusting member. Furthermore, an adjusting knob is provided that can be detachably attached to the adjusting member with an essentially positive fit.

15 Claims, 6 Drawing Sheets

EXTERNAL MOUNTING DEVICE, PARTICULARLY FOR EXTENSION OF A DISTANCE BETWEEN CLAMPING ELEMENTS

FIELD OF THE INVENTION

The invention relates to an external fixation device, particularly for the extension of the distance between two clamping members. It further relates to such a fixation device for osteosynthesis and, for example, to the use thereof for an external fixator.

More particularly, it relates to an external fixation device for the extension of the distance between two clamping elements for an external fixator having a central internal rod, with an outer hollow housing, in which internal rod is movable axially. One end of internal rod projects over the one end of the housing, and with an adjusting or drive member, that is disposed at the other end of the housing and that is connected with internal rod and/or the outer hollow housing, whereby the axial position of internal rod can be adjusted in relation to the housing by means of rotation of the adjusting member.

BACKGROUND OF THE INVENTION

A similar device is known from FR 2,557,933. It is used particularly in the context of an external fixator. It comprises a rectangular internal rod and a hollow tube surrounding the same, which are thus movable in one another in a torsion-resistant manner. The adjustment is to be made by means of a nut and an adjusting screw, disposed at the free end of the hollow tube. At the two ends of the device, a clamping member is or will be attached that is connected to the bone fragments by means of rods or pins. A clamping member is attached to the hollow tube by means of a bracket that is thus resistant to torsion in relation to the axis of the rectangular tube. At the free end of the interior shaft, an additional clamping member is attached through a longitudinal screw that can be screwed into internal rod, which is thus freely rotatable in relation to the axis of the rectangular internal rod. Non-metallic materials are used as the material for disposable use. After fixation of two facing bone fragments with two clamping members, it is possible, by means of actuation of the adjustment device, i.e., the nut and adjusting screw, to extend the distance between the attachment points of the fixator to the bone, i.e., to extend the length of the bone overall.

Another such device is known from U.S. Pat. No. 5,454,810. This publication targets the problem of the use of a rotationally-symmetrical inner rod and outer tube in relation to rotatory stability. In U.S. Pat. No. 5,454,810, a round outer tube with a bore of continuous square cross-section is used so that an internal rod with a square cross-section can be used in the outer tube. The outer tube is composed of two aluminum halves while the inner rod is made of steel. To avoid jamming, the prior art uses polymeric material strips in the bore.

The free end of the inner rod ends in a larger diameter part projecting out from the outer tube. This end serves to fix the one clamping member. The other end of the inner rod in the telescoping version of the device according to U.S. Pat. No. 5,454,810, shown with members in FIG. 8 therein, connects with a slide that is axially movable by means of a screw thread.

Other such devices are shown in U.S. Pat. Nos. 5,275,599 and 4,475,546.

These devices present the disadvantage that they are difficult to adjust because both publications refer to the operating surgeon effecting adjustments. The fixation knobs at the free ends, in contrast to this, can also be actuated unintentionally by the patients both in the hospital and under outpatient treatment and can thus be misadjusted.

One disadvantage of existing devices of this type therefore lies particularly in the fact that they are not simple to use. They should, advantageously, be changeable to a defined extent by the user as well, e.g., a patient should be able to extend said distance, i.e., said bone length, him/herself, in the simplest manner. At the same time, the device should be protected against unintentional actuation.

SUMMARY OF THE INVENTION

One aspect of the invention therefore relates to the task of improving a device of the above-mentioned type such that the device is simple to adjust to a defined extent, particularly by the patient him/herself. At the same time, it should be better protected against unintentional misadjustments.

The task is solved, according to the invention, by an adjusting knob that can be detachably attached to the adjusting member with an essentially positive fit. The attached adjusting knob can be placed in contact with at least one area of the housing. Adjusting knob and housing each have at least one complementary stop member so that a stop position with an altered length can be reached through the number and arrangement of the complementary stop members according to a predefined angle of rotation of adjusting knob.

A "stop" here is not an absolute halt in the sense of a lock on the device, but rather a location preventing rotation that can be overcome by minimal force, which facilitates a tactile experience for the user executing the rotation. The one end of internal rod projects beyond the one end of the housing and thus serves to fix a clamping member, while the housing serves to fix the other clamping member. A rotation in the one direction leads to an extension of the changed length while a rotation in the other direction leads to a retraction. Both changes are possible.

The device is smaller overall due to the fact that adjusting knob can be removed. This makes it easier for the patient to use the device to extend the distance between the bones, particularly on a daily basis.

Provision of a hanging device on the device, particularly in the form of a loop, is advantageous.

The problem is solved, in relation to the solution of the device as a whole according to the invention by an adjusting member having a rod with an external thread, an internal rod that is at least partially hollow and has an internal thread at its hollow end into which the external thread penetrates. The internal rod and housing have a torsion-resistant cross-section complementary to each other, and the adjusting member and the housing have a complementary conforming stop member to lock the adjusting member connected with internal rod and the housing against direct axial displacement.

"Lock" here is defined as the immobilization of the device that avoids a shortening of the distance between the clamping members.

A method for the use of the device according to the invention is presented.

Various aspects of the invention are provided by an extendable external fixation device which has a housing with an internal bore and a bone pin holder fixably mounted on an external surface of the housing. A telescoping member having a threaded inner bore and a bone pin holder fixably mounted thereon is slidably received within the bore of the housing. The bone pin holder is attached at a first end of the telescoping member opposite the end inserted into the housing. An anti-rotation element which may be in the form of polygonal cross-sections for the housing and telescoping member is utilized to prevent the relative rotation between the two. A drive member is rotatably mounted on a second end of the housing, which drive member has a threaded outer surface threadably received within the inner bore of the telescoping member whereby rotation of the drive member causes relative movement between the telescoping member and the housing. The drive member has an end spaced from the second end of the housing which includes a removable drive knob. Thus, the knob can be selectively engaged and disengaged from the drive head of the drive member. The housing has an outwardly facing circumferential recess for engaging at least one spring loaded detent element mounted on the drive knob. Preferably, the spring loaded detent elements are mounted in an external groove on the drive knob and extend through bores in the knob into engagement with the recesses in the housing. An O-ring or other spring element is mounted in or adjacent the groove and acts on the detent elements to provide the spring loading. Preferably, the telescoping member includes indicia such as a calibrated scale indicating the length of the external fixator as it expands and contracts via rotation of the knob when it is engaged on the drive head. Preferably, the drive head has four sides with coated indicia such as dots on each of the four sides. The indicia are visible when the drive knob is removed from the drive head.

BRIEF DESCRIPTION OF THE DRAWINGS

An embodiment of the invention is now explained in greater detail based on the drawings, as an example. They show.

DESCRIPTION

Figure 1:
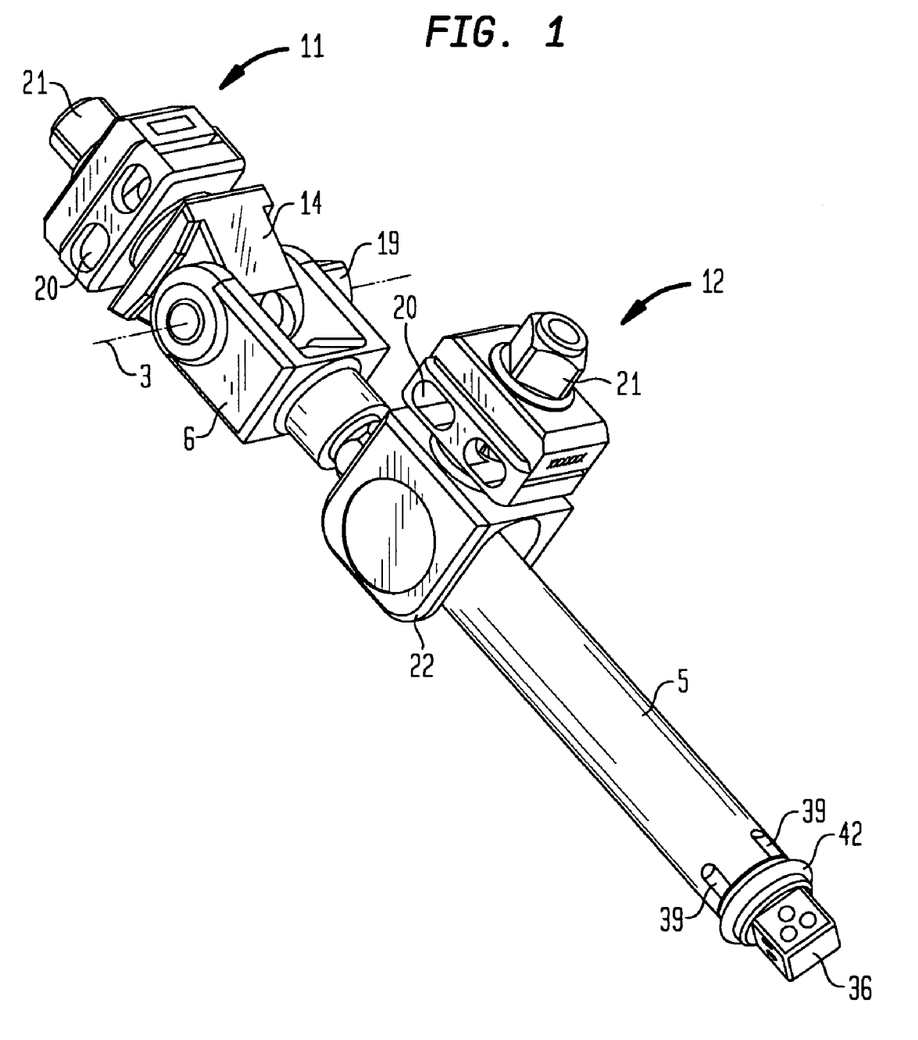
FIG. 1 is a perspective view of a device according to an embodiment of the invention with a clamping member attached thereto.

Referring to FIG. 1 there is shown a perspective view of an external fixation device 1 according to a preferred embodiment of the invention with an external second clamping member 12 attached thereto. A rod-like member such as a bone-pin (not shown) is attached to this external second clamping member 12 by the use of the device, which rod-like member is attached to a bone fragment. Reference number 11 designates a first clamping member disposed essentially in extension of the device 1, to which first clamping member 11, an additional rod-like member can be attached as well. This additional rod-like member is attached to another bone fragment by the use of the device, for example such that between the above-mentioned bone fragment and this bone fragment there is a gap whose length can be extended with this device.

Figure 3:
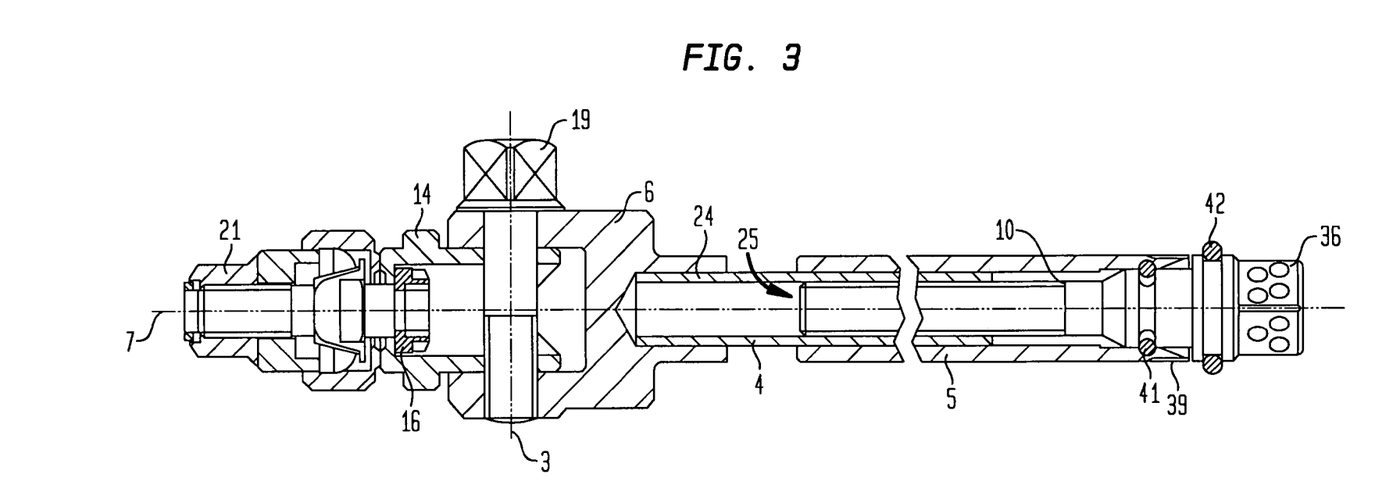
FIG. 3 is a partial cross-sectional view of the device according to FIG. 1, showing a housing without the external clamping member.

Such an external fixation device 1 for extension of a distance between the bone fragments attached to clamping members 11, 12 has, for an external fixator, a central internal rod 4, that is first properly visible in FIG. 3, since it is disposed in an outer hollow housing 5 of device 1. In this housing 5, internal rod 4 is movable axially indirectly by means of a first adjusting member 10, shown first in FIG. 3. Here, one end of internal rod 4 projects beyond the one end of housing 5 and is connected in the embodiment shown with a bracket 6 to which first clamping member 11 is rotatably fixed. Device 1 also has an adjusting member 10, shown in FIG. 7, which can be attached to the other end of housing 5, wherein an engagement knob 36, square in cross-section, is disposed, whose function is described in the following drawings in greater detail. The axial position of internal rod 4 can be adjusted in relation to housing 5 by means of the adjusting member.

Figure 2:
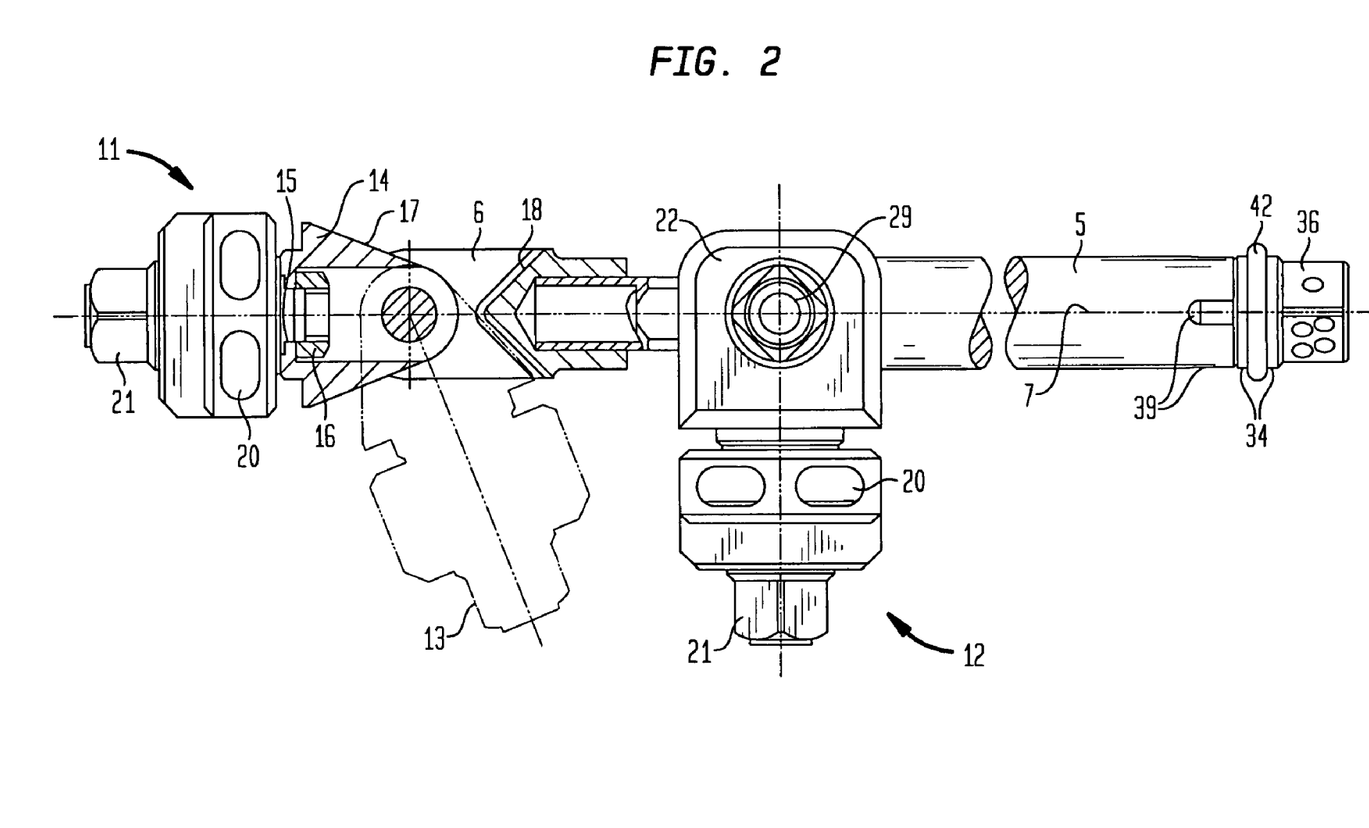
FIG. 2 is a partial cross-sectional view of the device according to FIG. 1.

First clamping member 11, in the embodiment shown, belongs entirely to device 1 and is rotatably connected with device 1 by means of an axle 3. In FIG. 2, a partial cross-section of the device according to FIG. 1 is shown. The same characteristics bear the same reference numbers in all drawings. First clamping member 11 can swivel around axle 3, for example for more than 90°, for example by 115° as here, until it reaches the position 13 shown by the dotted line in FIG. 2. A hollow body 14 is attached to the axle 3, in which a bore 15 is disposed in the radial direction thereof, into which first clamping member 11 can be inserted and clamped. A screw 16 can be used in the bore 15 for this purpose. Hollow body 14 has lateral stop edges 17, which, with the corresponding stop edges 18 of the bracket 6, limit the rotational movement of the clamping member 11 around the axle 3. Hollow body 14 is attached in a defined angular position by means of a clamping member 19, for example, a screw, which penetrates into the bracket 6.

In another embodiment not shown in the drawings, the extension of internal rod 4 can have a cylindrical member with the cross-section of housing 5. It is thus possible to use an additional second clamping member 12 as the "first" clamping member instead of the integrated first clamping member 11, as described below.

Second exterior clamping member 12 is attached to housing 5 of device 1 by means of a bracket 22. The shanks of the bracket encompassing housing 5 are tensioned against the housing by a clamping screw 29. Rod 4 runs in housing 5. Internal rod 4 can be moved longitudinally in relation to housing 5 by members 2, 10 described below so that the first clamping member 11 can move in relation to the second clamping member 12. Here, the clamping members 11 and 12 perform a translational movement in relation to each other, even if the axles of the bone pins or rods clamped by clamping members 11, 12 need not be aligned parallel to each other. With the clamping members 11 and 12 shown here as examples, the rods are each used in the openings 20 and fastened by the clamping screws 21.

FIG. 3 shows a partial cross-section view of the device 1 according to FIG. 1, without an external clamping member 12. The clamping member 21 is fixed in position with the screw 16 of the clamping member 11. The function of the clamping screw 19 is very easy to describe, since it compresses bracket 6 and thus clamps and fixes hollow body 14.

Figure 4:
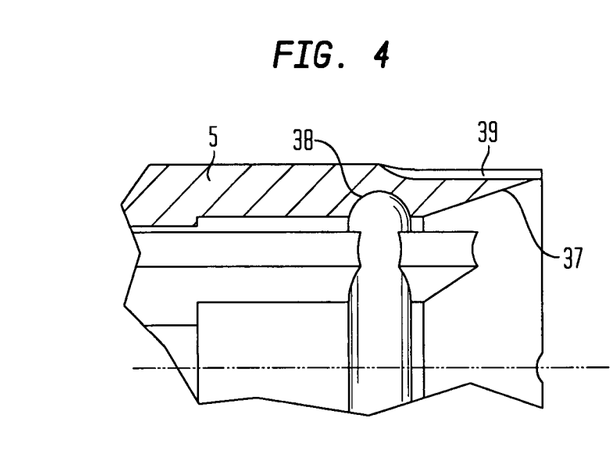
FIG. 4 is an enlarged sectional view of one end of the housing of FIG. 3.
Figures 5, 6:
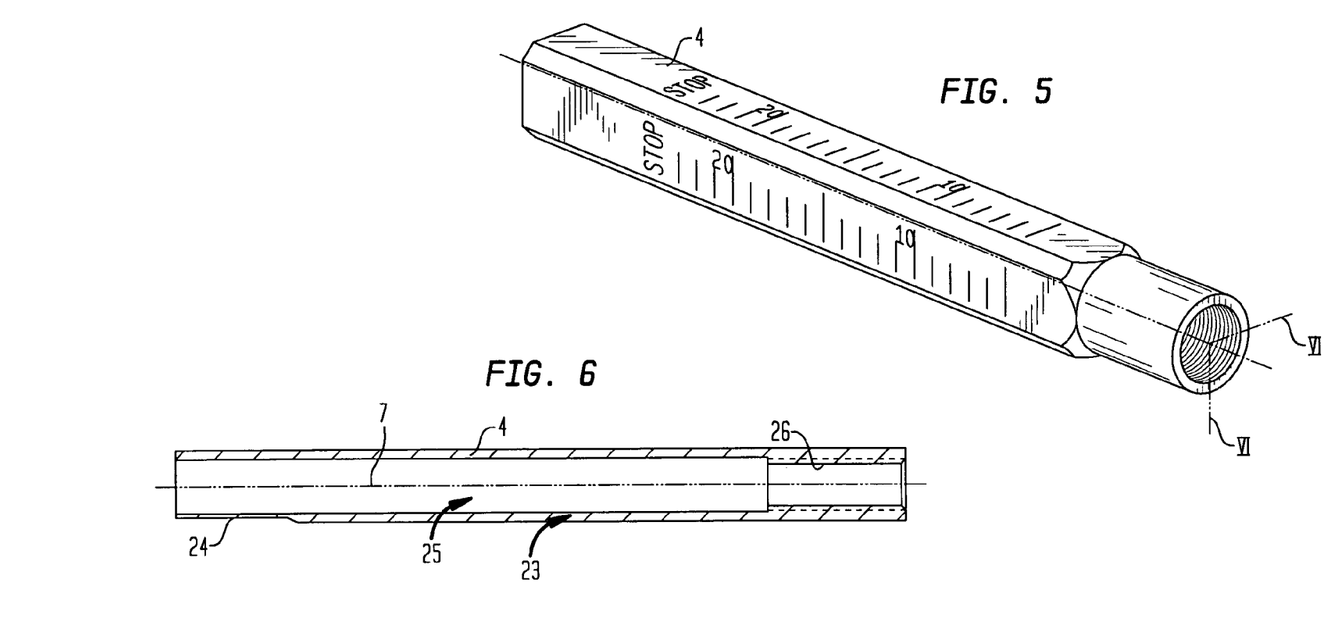
FIG. 5 is a perspective view of internal rod.
FIG. 6 is a cross-sectional view of internal rod along Lines VI-VI in FIG. 5.
Figure 7:
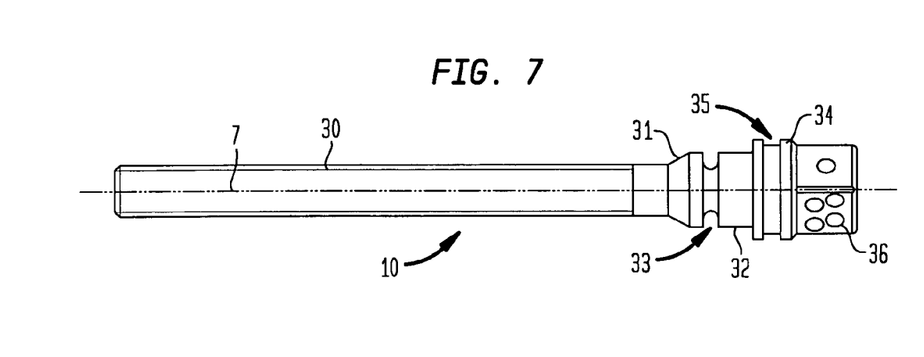
FIG. 7 is a side view of the adjusting member.

The following description is to be viewed in connection with FIG. 4, which shows an enlarged sectional view of the one end of housing 5, with FIG. 5, which shows a perspective view of internal rod 4, with FIG. 6, which shows a cross-section view of internal rod 4 according to Lines VI-VI of FIG. 5, and with FIG. 7, which shows a side view of the adjusting member 10.

Housing 5 has an essentially square bore that is designed to be complementary to outer shell 23 of internal rod 4. The outer shell 23 is provided, on its flat side, with a readable scale. Here, the value of the scale mark above housing 5 is to be read. Interior rod 4 is formed at its end into a cylinder 24 so that it can be attached in bracket 6. The section shown in FIG. 3 corresponds to a top view of a rectangular side of internal rod 4.

Interior rod 4 is designed to be hollow. The cylindrical interior bore 25 is preferably continuous, but can also end as a blind hole in the area of reduced cylinder 24. At the end facing the cylinder 24, internal rod 4 is designed internally with an internal thread 26 whose exterior diameter is at least not larger than the internal diameter of the interior bore 25, so that the adjusting member 10 can be inserted into rod 4 by means of thread 26.

The adjusting member 10 has a threaded rod 30 of sufficient length, where the length, together with the dimensions of housing 5 and internal rod 4, determine the total travel of the telescoping function. The thread 26 and the complementarily threaded rod 30 are advantageously designed with a very fine thread so that a number of rotations are necessary to reach a given translational travel.

A conical expansion 31 element connects to this threaded rod 30 after a short unthreaded section, which expansion element evolves into a cylindrical section 32 of a larger diameter, in which a circumferential circular groove is provided. Broadening out like a flange, an additional cylindrical section 34 of a larger diameter is connected, in which an additional groove 35 is provided. Finally, the engagement knob 36 connects to section 34, which knob preferably has a square cross-section in the top view along axis 7. Each side of the knob 36 has a coding of holes, like spots on dice, in a number from one to four. Thus, a flat wrench can be used and the further rotation of the spots is each counted as a quarter-turn. The user can also recognize the direction of rotation for the extension function from the increasing number of spots.

FIG. 3 shows that a retaining ring 41 is inserted into the groove 33, which ring is inserted into the internal groove 38 of housing 5 through the sliding edges 37. The additional lines in FIG. 4 belong to the square receptacle 4. After insertion of the retaining ring 41 into the groove 38 in the housing, the shoulder also comes into contact between sections 32 and 34, near housing 5. The first O-ring 42 is inserted into the groove 35 in section 34. One the outside of housing 5, at a regular angular pitch of 90°, a groove 39 is chamfered on the running surface, which is also a rounded recess in the direction of the circumference of housing 5, whose function will be made clear in connection with the stop member 8. The retaining ring 41 can, for example, be a steel spring that holds members 5 and 10 apart at a fixed distance. Thus, only internal rod 4 is moved axially by the rotation of member 36.

Figure 8:
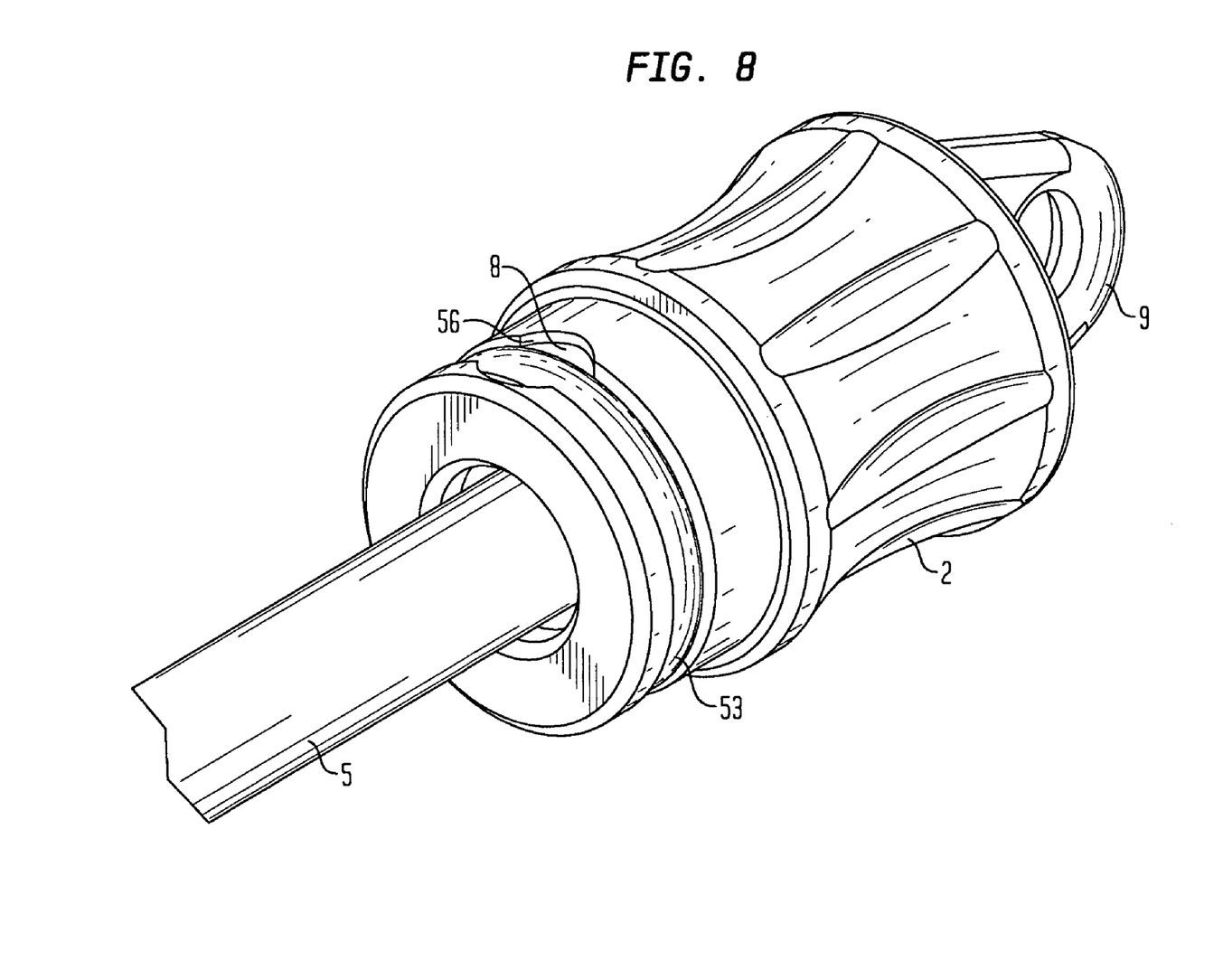
FIG. 8 is a perspective view of adjusting knob.
Figure 9:
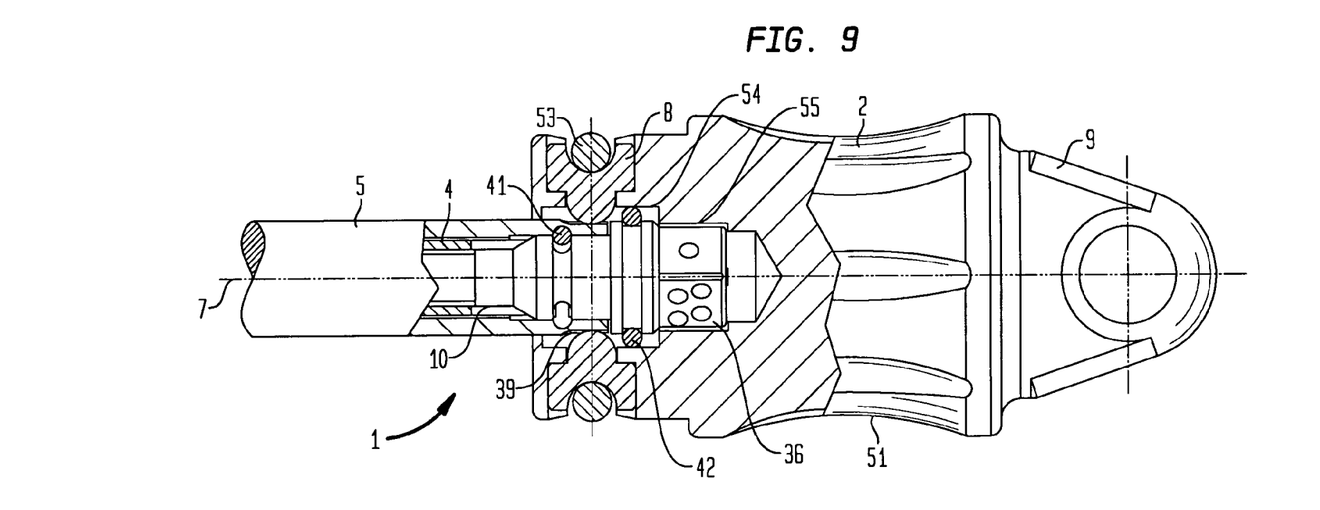
FIG. 9 is a partial cross-sectional view of the device according to FIG. 1 with an adjusting knob according to FIG. 8 mounted thereon.
Figure 10:
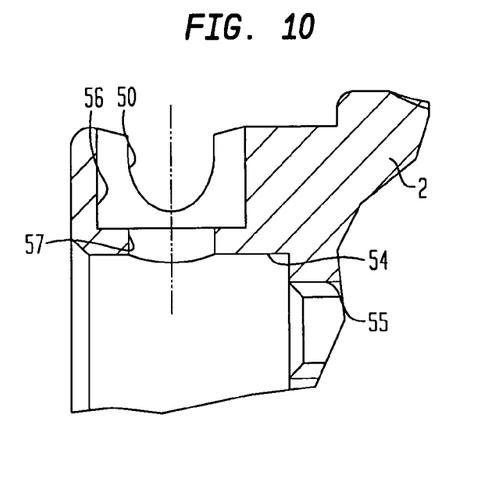
FIG. 10 is an enlarged view of the rotary groove on the adjusting knob.
Figure 11:
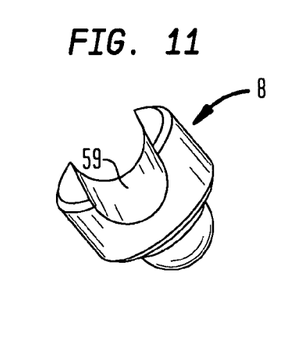
FIG. 11 is a perspective view of a stop member of the adjusting knob.
Figure 12:
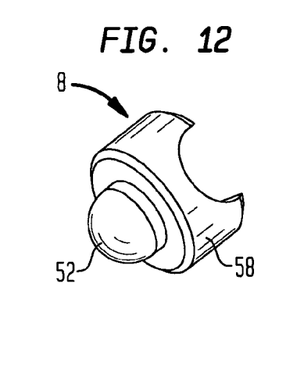
FIG. 12 is a second perspective view of a stop member of the adjusting knob.

FIG. 8 shows a perspective view of adjusting knob 2. FIG. 9 shows a partial cross-section of the device according to FIG. 1 with adjusting knob 2 according to FIG. 8. FIG. 10 shows an exploded view of the rotary groove 50 of adjusting knob 2. FIGS. 11 and 12 show two perspective views of the stop member 8 of adjusting knob 2. In connection with the description of these figures, the method of functioning of the device will also be explained.

On the left side of the drawing in FIG. 9, housing 5 can be seen, in which internal rod 4 and the adjusting member 10 run.

Adjusting knob 2 has an engagement area 51 for the user. At its end on the engagement side, it has a two-stage internal bore 54 and an internal square shaft 55 for acceptance of the first O-ring 42 or the engagement knob 36. Essentially, the O-ring 42 is intended to hold the clamping device 12, which can thus be disposed on housing 5 and cannot be lost when the device is being handled.

The rotary groove 50 is disposed in the adjusting knob 2 outside the internal bore 54, which groove has a two-stage bore 56 and 57 running radially at two facing points. The first layer stage 56 expands and deepens the rotary groove 50. The second stage 57 forms a through-bore into the internal bore 54. A second O-ring 53 is inserted into the rotary groove 50. Prior to this, however, stop members 8 are inserted into bores 56, 57. These stop members have, as shown in FIGS. 11 and 12, a cylindrical upper area 58 and a lower hemispherical projection 52 of small diameter. Here, the cylindrical upper area 58 fits in the first stage of bore 56 and projection 52 can penetrate into the second stage 57 of the bore. Stop members 8 are held in their receptacles by the O-ring 53 and are pressed against the shoulder between the sections 56 and 57 of differing diameter. Stop members 8 have a groove 59 for this purpose, through which the O-ring 53 runs. Instead of two stop members 8, for example, three can be disposed with an angular pitch of 120° or even four at 90°. Other numbers and angular distributions are also possible.

Instead of the separate bolt-like stop members 8 held by the second O-ring 53, adjusting knob 2 can also have bosses corresponding to the hemispherical projections 52 by means of tongues, which bosses penetrate into grooves 39 on the running surface, so that the user has a tactile experience. Otherwise, housing 5 can also be provided with one or a plurality of embossments that are pressed apart by the corresponding conforming hollow cylindrical segments of adjusting knob 2, wherein grooves in adjusting knob 2 provide a palpable stoppage. It is also possible to use individual balls directly instead of the stop members 8 with the hemispherical projections 52, which ball-shaped projections run in the retainer formed by the edges 56.

The device is used in two steps. The operating physician fixes the external fixator in the broken bone with the corresponding fixations formed of rod-like members each as bone pins, either directly on the device 1 or indirectly to it. Here the surgeon attaches adjusting knob 2 to engagement knob 36. While attaching adjusting knob 2, the stop members 8 slip against the first O-ring 42 and over it. Thus, the knob 2, after fixation, is secured against axial displacement and unintentional falling out. In other embodiments not shown in the drawings, this can be achieved if a circular flexible member on the inside 54 of engagement knob 2, similar to the O-ring. 42, is provided to form, together with the above-mentioned stop members (then on housing 5), an axial protection against removal for the engagement knob 2.

The engagement knob 36, shaped like a die, then slides into the complementary square internal bore 55, which has some play, so that a positive fit is achieved. The physician now adjusts the initial distance by rotating knob 2 to achieve the desired spatial relationship between the rods holding the bones. It should be emphasized that this adjustment is subsequently fixed. An unintentional rotation of device 1 is also precluded by the tubes 4 and 5, placed one inside the other and torsion-resistant. By means of the three-stage longitudinal adjustment with members 4, 10, and 5, a secure immobilization of the desired distance is ensured, which cannot be misadjusted unintentionally, particularly if the physician removes adjusting knob 2. Adjusting knob 2 can be equipped with a hanging device 9 that has a hole to pass a cord through, for example.

The current adjustment can now be read off the scale marking on internal rod 4. The travel, and therefore the change in distance between clamping members 11 and 12 is determined by the screw threads 26/30, by the rotation or partial rotation of adjusting knob 2. Thus, the patient can make the subsequent corresponding adjustments him/herself, at the doctor's orders. The patient receives an adjusting knob 2 for this purpose. If such knob is not attached, the device is secured against unintentional changes in the adjustment, as stated above. A marking assigned to stop member 8 is advantageously placed on adjusting knob 2, which is attached to housing 5 opposite a groove 39 on the running surface. Thus, adjusting knob 2 can be permanently attached. After attachment of adjusting knob 2, the patient can carry out a defined, simple, reproducible rotation of the knob 2. With preferably two opposing stop members 8 and preferably four grooves 39 on the running surface, the patient feels a stop after completion of a 90° turn. With correspondingly fine threads, changes in the length of the bone can be adjusted at predefined intervals. For example, the patient can be instructed to make three full turns every second day, i.e., turning the knob until the patient feels a catch with members 8 and 39 twelve times.

With three stop members 8 and one single groove 39 on the running surface or three grooves 39 on the running surface set at a pitch of 120°, the angular resolution of one rotation is equal to 120°. If three stop elements 8 are assigned to two opposing grooves 39 in the running surface, the angular resolution comes to 60°. The same resolution is achievable with two stop members 8 as in the present embodiment and six grooves 39 on the running surface. The person skilled in the art can see additional possibilities as needed. After removal of adjusting knob 2, there are no members projecting beyond the rod, so that an accidental adjustment is unlikely. To ensure the adjustment, a hollow cylindrical protective housing can be pushed on over adjusting knob 2 on housing 5, which is held by the first O-ring 42, whose rotation by means of the rotating of such a housing does not cause the adjusting member 10 to rotate. In control tests, the scale on internal rod 4 permits reading and thus a check on the number of rotations made, i.e., the change in length effectuated.

The material selected for the components of housing 5 and internal rod 4, adjusting member 10, and the other members can be steel such as stainless steel so that steel-to-steel contact surfaces can be formed.

The embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings, which embodiments fall within the framework of the scope of protection requested in the present claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An extendible external fixator comprising:
a housing having an internal axially extending bore and a bone pin holder mounted on an external surface thereof;
a telescoping member having a threaded inner bore and a bone pin holder mounted thereon spaced from a first end of said housing slidably received in said bore of said housing;
means for preventing relative rotation between said housing and said telescoping member; and
a drive member rotatably mounted on a second end of said housing and having a threaded outer surface threadably received within said inner bore of said telescoping member whereby rotation of said drive member causes relative movement between said telescoping member and said housing, a drive knob having at least one spring loaded detent element movable in a direction perpendicular to the axial bore upon rotation of the drive member the at least one spring loaded detent element moves into engagement with a plurality of corresponding stop members located on an outer surface of the housing to extend the fixator in predefined intervals wherein the drive knob is selectively engagable with the drive member.

2. The external fixator as set forth in claim 1 wherein the at least one spring loaded detent element is mounted on the drive knob.

3. The external fixator as set forth in claim 2 wherein said housing has outwardly facing circumferential recesses acting as stop members for engaging the at least one spring loaded detent element mounted on said drive knob.

4. The external fixator as set forth in claim 3 wherein the at least one spring loaded detent elements is mounted in an external groove in the drive knob and extend through a bore in the drive knob into engagement with the recesses in the housing.

5. The external fixator as set forth in claim 4 wherein an O-ring is mounted in a groove on said at least one spring loaded detent element and acts on said at least one detent element to provide said spring loading.

6. The external fixator as set forth in claim 1 wherein said telescoping member includes indicia indicating the length of said external fixator.

7. The external fixator as set forth in claim 1 wherein said drive member has four sides with coded indicia on each side.

8. The external fixator as set forth in claim 7 wherein the indicia are dots.

9. An extendible external fixator comprising a central internal rod and an outer axially extending hollow housing having a bone pin holder, the internal rod movable axially within the housing, whereby a first end of the internal rod projects over a first end of the housing, and further comprising an adjusting member disposed at a second end of the housing connected with the internal rod and the outer hollow housing, whereby the axial position of the internal rod can be adjusted in relation to the housing by means of rotation of the adjusting member, wherein a drive knob is detachably attached to the adjusting member, and wherein the attached drive knob can be placed in contact with at least one area of the housing and wherein the drive knob and housing each have at least one complementary stop member, one of which is a spring detent element so that a stop position with an altered length can be reached and felt by a user through the number and arrangement of the complementary stop members according to a predefined angle of rotation of the drive knob, the detent element movable in a direction perpendicular to the axial bore into engagement with a corresponding stop member upon rotation of the drive knob to extend the fixator in predefined intervals.

10. The extend fixator as set forth in claim 9 wherein the housing has a plurality of recesses or embossments disposed at a regular angular intervals acting as the stop members and wherein the drive knob has one or a plurality of embossments or recesses, disposed at a regular angular intervals acting as the stop members.

11. The external fixator as set forth in claim 10 wherein the embossments on drive knob are heads projecting from an axial recess, formed by members held by elastic force of an O-ring.

12. The external fixator as set forth in claim 9 wherein, on the outside of the housing or on the inside of the drive knob, a circumferential flexible member is disposed to form, with the stop members, an axial removal protection for the drive knob.

13. The external fixator as set forth in claim 9 wherein the drive knob is provided with a hanging device, particularly a loop.

14. An extendable fixator device comprising first and second clamping members, a central internal rod, an outer hollow housing, the internal rod movable axially within the housing, one end of internal rod projects over a first end of the housing, and further comprising an adjusting member, disposed at a second end of the housing and operatively connected to the internal rod and to the outer hollow housing, whereby the axial position of the internal rod can be adjusted in relation to the housing by means of rotation of the adjusting member, wherein the adjusting member has a rod with an external thread, the internal rod is at least partially hollow and has an internal thread into which said external thread of the adjusting member penetrates, and wherein the internal rod and housing having a torsion-resistant cross-section cooperating with each other, the adjusting member and the housing have a complementary conforming stop member to lock the adjusting member connected with internal rod and the housing against direct axial displacement, and a drive knob mounted on the housing for rotating the adjusting member in predefined angular intervals, the drive knob including a spring detent element engagable with a plurality of stop members on the housing whereby rotation of the drive knob adjusts the length of the fixator in predefined intervals.

15. The external fixator as set forth in claim 14 wherein the spring detent is mounted on a drive knob which is selectively engagable with the adjusting member.

* * * * *

UNITED STATES PATENT AND TRADEMARK OFFICE
CERTIFICATE OF CORRECTION

PATENT NO. : 7,632,271 B2 Page 1 of 1
APPLICATION NO. : 11/119574
DATED : December 15, 2009
INVENTOR(S) : Baumgartner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 963 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,632,271 B2 |
| APPLICATION NO. | : 11/119574 |
| DATED | : December 15, 2009 |
| INVENTOR(S) | : Thomas Baumgartner and Andreas Bernhard |

It is certified that error appears in the above-identified patent and that said Letters Patent is hereby corrected as shown below:

On the Title Page, Item (57), under Abstract, line 7, "connected with" should read --connected with the--.
Column 1, line 16, "which internal" should read --which the internal--.
Column 1, line 17, "of internal" should read --of the internal--.
Column 1, line 18, "member, that is" should read --member that is--.
Column 1, line 20, "with internal" should read --with the internal--.
Column 1, line 39, "screwed into internal" should read --screwed into the internal--.
Column 2, line 23, "Adjusting knob" should read --The adjusting knob--.
Column 2, line 27, "of adjusting knob" should read --of the adjusting knob--.
Column 2, line 31, "one end of" should read --one end of the--.
Column 2, line 38, "that adjusting" should read --that the adjusting--.
Column 2, line 45, "invention by" should read --invention, by--.
Column 2, lines 52-53, "with internal" should read --with the internal--.
Column 3, lines 12-13, "spring loaded" should read --spring-loaded--.
Column 3, line 14, "spring loaded" should read --spring-loaded--.
Column 3, line 42, "of internal" should read --of the internal--.
Column 3, line 43, "of internal rod along Lines" should read --of the internal rod along lines--.
Column 3, line 46, "of adjusting" should read --of the adjusting--.
Column 5, line 3, "Lines" should read --lines--.
Column 5, line 29, "expansion 31 element" should read --expansion element 31--.
Column 5, line 50, "One" should read --On--.
Column 6, line 63, "the other and" should read --the other, which are--.
Column 8, lines 16-17, "spring loaded" should read --spring-loaded--.
Column 8, lines 18-19, "member" should read --knob,--.
Column 8, line 19, "spring loaded" should read --spring-loaded--.
Column 8, line 26, "spring loaded" should read --spring-loaded--.
Column 8, line 31, "spring loaded" should read --spring-loaded--.
Column 8, line 34, "spring loaded detent elements" should read --spring-loaded detent element--.

Signed and Sealed this
First Day of March, 2011

David J. Kappos
*Director of the United States Patent and Trademark Office*

CERTIFICATE OF CORRECTION (continued)

U.S. Pat. No. 7,632,271 B2

Column 8, line 35, "extend through" should read --extends through--.
Column 8, lines 39-40, "spring loaded" should read --spring-loaded--.
Column 9, line 5, "at a regular" should read --at regular--.
Column 9, line 7, "at a regular" should read --at regular--.
Column 9, line 10, "on drive" should read --on the drive--.
Column 9, line 24, "end of internal" should read --end of the internal--.
Column 10, line 10, "housing having" should read --housing have--.